United States Patent [19]

Faggian et al.

[11] Patent Number: 4,778,945
[45] Date of Patent: Oct. 18, 1988

[54] PROCESS FOR REMOVING PARAFFINS FROM THEIR MIXTURES WITH PARAFFINSULPHONIC ACIDS

[75] Inventors: Lucio Faggian, San Donato Milanese; Cosimo Franco, Locri, both of Italy

[73] Assignees: Eniricerche S.P.A., Milan; Enichem Augusta S.P.A., Palermo, both of Italy

[21] Appl. No.: 71,871

[22] Filed: Jul. 10, 1987

[30] Foreign Application Priority Data

Jul. 23, 1986 [IT]  Italy ............................... 21223 A/86

[51] Int. Cl.$^4$ ........................... C07C 7/00; C10G 31/00
[52] U.S. Cl. ................................. 585/802; 208/263; 260/513 R; 585/811
[58] Field of Search ............. 585/802, 811, 856; 260/513 R; 208/263

[56] References Cited

U.S. PATENT DOCUMENTS 3,988,218 10/1976 Suzuki et al. .................. 260/513 R
4,568,447  2/1986 Pujado et al. ........................ 208/263

FOREIGN PATENT DOCUMENTS 2033144 2/1987 Japan ................................ 260/513 R
6812646 3/1970 Netherlands ..................... 260/513 R

*Primary Examiner*—Asok Pal
*Attorney, Agent, or Firm*—Morgan & Finnegan

[57] ABSTRACT

Mixtures of $C_{12}$–$C_{18}$ n-paraffins with paraffinsulphonic acids having the same number of carbon atoms, water and sulphuric acid, and obtained by sulphoxidation of said paraffins with $SO_2$ and $O_2$ in the presence of water and UV radiation are stripped of their excess $SO_2$ and decanted to separate most of the paraffins, and obtain a residual mixture. The residual mixture is dehydrated according to the invention until a two-phase system forms or at least until the mixture becomes turbid, and the dehydrated mixture either as such or after separating the heavier phase consisting of water and sulphuric acid is extracted with supercritical $CO_2$, which removes with it the n-paraffins, these being reused in the sulphoxidation process.

4 Claims, 1 Drawing Sheet

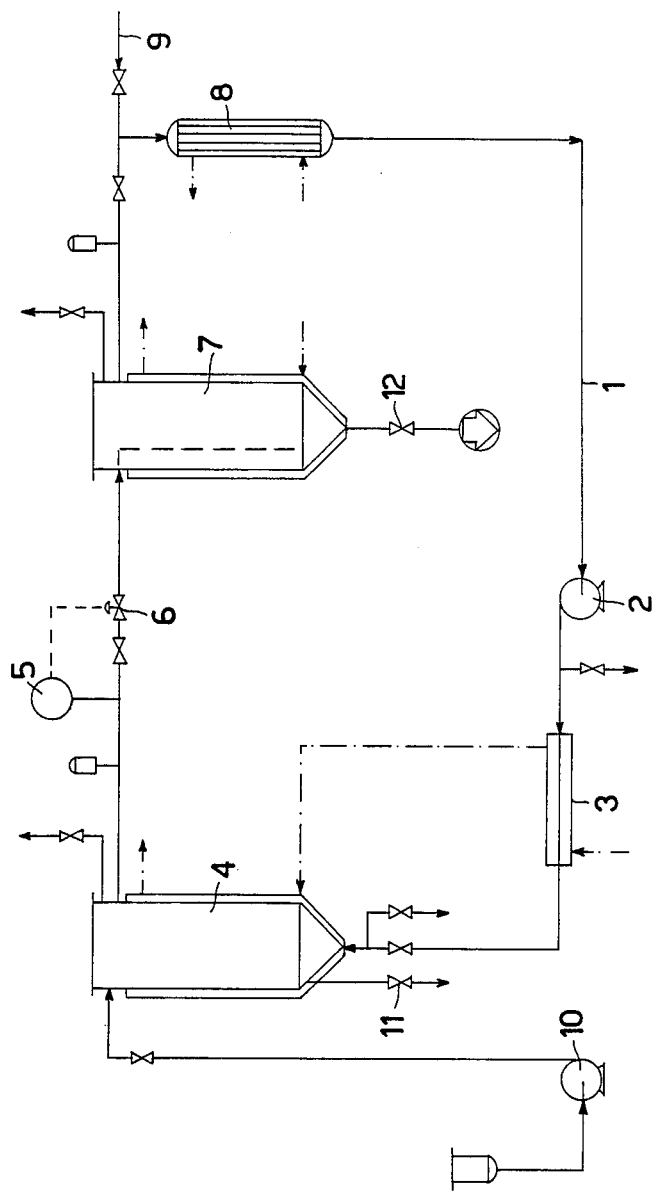

PROCESS FOR REMOVING PARAFFINS FROM THEIR MIXTURES WITH PARAFFINSULPHONIC ACIDS

This invention relates to a process for removing n-paraffins from their mixtures with paraffinsulphonic acids. Paraffinsulphonic acids containing between 12 and 18 carbon atoms are generally prepared by sulphoxidation of $C_{12}$–$C_{18}$ paraffins with $SO_2$ and $O_2$ using UV radiation for reaction initiation. The reaction product obtained form the sulphoxidation reactor consists of a mixture containing small percentages of paraffinsulphonic acids, water and sulphuric acid, but mostly unreacted n-paraffins.

Most of the n-paraffins can be easily separated from said mixture, but a substantial fraction of them remains together with the sulphuric acid, the water and the paraffinsulphonic acids. It is important to note that the n-paraffins must be separated to the maximum possible extent not only for obvious economic reasons, but also because their presence in paraffinsulphonic acids is undesirable.

The known art gives suggestions for separating n-paraffins from the rest of the sulphuric acid, paraffinsulphonic acid and water mixture, one of these suggestions being contained in European patent application No. 131913, in particular in Example 1, according to which the mixture containing paraffinsulphonic acids, unreacted n-paraffins, water and sulphuric acid is treated with isopropanol in a quantity of 15%, to separate the mixture into three distinct phases, the upper one essentially consisting of n-paraffins, the lower one consisting of water, sulphuric acid and isopropanol, and the intermediate one containing paraffinsulphonic acids, sulphuric acid, water, n-paraffins and isopropanol. The intermediate phase is then mixed with methylene chloride to separate an aqueous sulphuric acid phase containing isopropanol and a little methylene chloride from a phase containing paraffinsulphonic acids, n-paraffins, water, methylene chloride and sulphuric acid, this being neutralised with soda and concentrated, and finally heated to a temperature of 200° C. to distill off the n-paraffins.

This procedure for removing the n-paraffins is obviously complicated, and notwithstanding its various extraction stages it is still necesary to use high-temperature vaporisation at the end, which in all cases damages the product obtained. With the known process it is therefore not possible to prepare free paraffinsulphonic acids or their salts with weak bases, as these are unstable at high temperature.

It has been surprisingly found that the previously described drawbacks of the known art regarding the separation of n-paraffins can be obviated in a very simple manner by dehydrating the mixture (partial removal of the water present) of $C_{12}$–$C_{18}$ n-paraffins, paraffinsulphonic acids, water and sulphuric acid, and then subjecting the dehydrated mixture to extraction with supercritical $CO_2$, this removing all or substantially all the n-paraffins.

The present invention provides a process for removing n-paraffins containing between 12 and 18 carbon atoms from mixtures of said n-paraffins with paraffinsulphonic acids having the same number of carbon atoms, water and sulphuric acid, where said mixtures have been obtained by sulphoxidation of $C_{12}$–$C_{18}$ n-paraffin mixtures at a temperature of between 25° and 50° C. with $SO_2$ and $O_2$ in the presence of water and UV radiation, comprising removing excess $SO_2$, if present, from the reaction mixture originating from the paraffinsulphonic acid synthesis reactor, and decanting the mixture to remove most of the $C_{12}$–$C_{18}$ n-paraffins, said process being characterised in that the residual mixture obtained after removing the $SO_2$ and the decanted paraffins is dehydrated until a two-phase system forms, or at least until the mixture becomes turbid, the dehydrated mixture then being extracted with supercritical $CO_2$, which removes all or substantially all the residual n-paraffins.

With regard to dehydration of the residual mixture, it should be noted that this must be continued at least until it becomes turbid, this being a sign of commencement of the formation of a two-phase system. The dehydration can be conducted until 85% of the water initially present in the mixture is removed. If dehydration is conducted beyond the formation of mixture turbidity, a two-phase system forms in which the lower heavier phase consists of water and sulphuric acid. The upper or supernatant phase is subjected to extraction with supercritical $CO_2$, and the lower phase (water + $H_2SO_4$) is removed.

Dehydration can be conducted with any medium which does not interfere with the system, and thus absorption systems can be used if they have high selectivity only towards water. However, the preferred system consists of controlled evaporation at a temperature less than 100° C., and preferably under vacuum at a temperature of 50° C. or less.

With regard to the conditions under which the dehydrated mixture is extracted with supercritical $CO_2$, these are as follows:
extraction temperature: between 32° C. and 80° C.
extraction pressure: between 75 and 350 bar
weight ratio of $CO_2$ used for extraction to paraffinsulphonic acids present in the dehydrated mixture: between 1:1 and 50:1.

The paraffinsulphonic acid mixture resulting from the process according to the present invention is then generally neutralised in known manner using chosen bases, to thus obtain paraffin sulphonates of any desired type.

The sulphuric acid contained in the mixture resulting from the process of the present invention can be separated, if required, by methods known in the art, such as mixing with suitable substances or precipitation to form insoluble salts.

An example is given hereinafter to better illustrate the invention, but without intending to limit the invention thereto or thereby.

EXAMPLE 200 g of a crude mixture (free of $SO_2$ and naturally decanted paraffins) of paraffinsulphonic acids, obtained by sulphoxidation of $C_{12}$–$C_{18}$ n-paraffins and having the following composition:
paraffinsulphonic acids: 24.74% by weight
$C_{12}$–$C_{18}$ n-paraffins: 26.46% by weight
water: 40.94% by weight
sulphuric acid: 7.86% by weight
were placed in the flask of a rotary evaporator.

Maintaining the temperature in the evaporation flask at less than 45° C. and operating under vacuum, water was distilled from this mixture until turbidity appeared in the evaporation flask. At this point, 38.5 g of water had been evaporated. Distillation was continued, and a further 7.5 g of water were evaporated. The residue in the flask consisted of two liquid phases. The lower phase, consisting of water and sulphuric acid, was separated (7.7 g). The upper phase (146.3 g) contained all the fed paraffinsulphonic acids and paraffins, and smaller quantities of water and sulphuric acid.

106.5 g of this mixture were fed into the extractor of the laboratory extraction apparatus described hereinafter, and were extracted with $CO_2$ under supercritical conditions.

The extraction temperature was maintained at 45° C., the extraction pressure at 150 bar and the $CO_2$ throughput at 1.72 kg/h. After two hours of extraction, the $CO_2$ feed was halted and the product contained in the extractor was discharged and analysed. Its composition was as follows:

paraffinsulphonic acids: 58.91% by weight
$C_{12}-C_{18}$ n-paraffins: 0.03% by weight
water: 28.90% by weight
sulphuric acid: 12.16% by weight The extracted paraffins, collected in the separator, were found to be pure and could be recycled to the sulphoxidation reactor without any treatment.

The extraction apparatus used in the example is shown in FIGURE.

BRIEF DESCRIPTION OF DRAWING

It consists of a refrigeration cycle for condensing $CO_2$ in the heat exchanger 8. The liquid $CO_2$ 1 is pumped by the diaphragm pump 2 to the preheater 3 and then to the extractor 4. The temperature of 3 and 4 is maintained constant and at the same value by circulating water from a temperature-controlled bath. The pressure in 4 is kept constant at the required value by the controller 5 and control valve 6.

The $CO_2$ containing the products extracted from the crude mixture fed into 4 passes through 6 and leaves the supercritical field in the separator 7, where the $CO_2$ evaporates and is condensed in 8 to then return to the already described cycle, whereas the extract remains in the separator. Any required make-up $CO_2$ is fed through 9.

The separator 7 is provided with two diametrically opposite sight glasses for visually checking the level. This is kept constant by adjusting the temperature of the water originating from a second temperature-controlled bath. The pressure in 7 is kept constant by a pressure switch which operates the refrigeration cycle. A cylindrical vessel with its top and base of porous sintered steel can be arranged inside the extractor 4, to receive the feed of crude product to be extracted. In the preferred embodiment, the extractor is filled with stainless steel packing held down by a demister.

A second pump 10 is used for continuous operation to feed the crude product to be extracted. In this case, the refined product is discharged through the valve 11.

We claim:

1. A process for removing nonsulfonated $C_{12}-C_{18}$ n-paraffins from a mixture of paraffinsulphonic acids, sulphur dioxide, sulphuric acid and water comprising:
   (a) removing substantially all of the sulphur dioxide from the mixture of n-paraffins, sulphuric acid, paraffinsulphonic acids and water, said mixture formed by sulphoxidation of the n-paraffins at a temperature of between about 25° C.–50° C. with sulphuric acid and oxygen in the presence of water and UV radiation;
   (b) decanting the mixture thereby removing substantially all of the n-paraffins and forming a second mixture comprised of sulphuric acid, paraffinsulphonic acids, water and residual n-paraffins;
   (c) dehydrating the second mixture thereby forming a first phase comprised substantially of the residual n-paraffins and paraffinsulphonic acids and a second phase comprised substantially of sulphuric acid and water; and
   (d) extracting substantially all of the residual n-paraffins from the first phase with supercritical $CO_2$ at a temperature ranging from about 32° C. to about 80° C.

2. A process as claimed in claim 1, wherein the dehydration is effected by controlled evaporation at a temperature less than 100° C.

3. A process as claimed in claim 2, wherein the dehydration is conducted under vacuum at a temperature of 50° C. or under hydrogen.

4. A process as claimed in claim 1, wherein the extraction with supercritical $CO_2$ is effected at a temperature of between 32° C. and 80° C., a pressure of between 75 and 350 bar and a weight ratio of $CO_2$ to paraffinsulphonic acids in the dehydrated mixture of between 1:1 and 50:1.

* * * * *